(12) United States Patent  
Laughner et al.

(10) Patent No.: US 9,730,603 B2  
(45) Date of Patent: Aug. 15, 2017

(54) MEDICAL DEVICES FOR MAPPING CARDIAC TISSUE

(71) Applicant: Boston Scientific Scimed Inc., Maple Grove, MN (US)

(72) Inventors: Jacob I. Laughner, St. Paul, MN (US); Shibaji Shome, Arden Hills, MN (US); Paul Hultz, Brookline, NH (US); Kevin J. Stalsberg, White Bear Lake, MN (US); Pramodsingh H. Thakur, Woodbury, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/744,888

(22) Filed: Jun. 19, 2015

(65) Prior Publication Data

US 2015/0366476 A1  Dec. 24, 2015

Related U.S. Application Data

(60) Provisional application No. 62/015,007, filed on Jun. 20, 2014.

(51) Int. Cl.
*A61B 5/044* (2006.01)
*A61B 5/042* (2006.01)
(Continued)

(52) U.S. Cl.
CPC ............ *A61B 5/044* (2013.01); *A61B 5/046* (2013.01); *A61B 5/04012* (2013.01);
(Continued)

(58) Field of Classification Search
CPC ....... A61B 5/044; A61B 5/0422; A61B 5/046; A61B 5/0464; A61B 5/6858;
(Continued)

(56) References Cited

U.S. PATENT DOCUMENTS

| 4,754,753 A | 7/1988 | King |
| 4,799,493 A | 1/1989 | DuFault |

(Continued)

FOREIGN PATENT DOCUMENTS

| CN | 101313334 A | 11/2008 |
| CN | 101317194 A | 12/2008 |

(Continued)

OTHER PUBLICATIONS

International Preliminary Report on Patentability issued in PCT/US2014/053147, mailed Mar. 10, 2016, 9 pages.

(Continued)

*Primary Examiner* — Paula J Stice

(74) *Attorney, Agent, or Firm* — Faegre Baker Daniels LLP

(57) ABSTRACT

Medical devices and methods for making and using medical devices are disclosed. An example medical device may include a system for mapping the electrical activity of the heart. The system may include a catheter shaft with a plurality of electrodes. The system may also include a processor. The processor may be capable of collecting a set of signals from at least one of the plurality of electrodes. The set of signals may be collected over a time period. The processor may also be capable of calculating at least one propagation vector from the set of signals, generating a data set from the at least one propagation vector, generating a statistical distribution of the data set and generating a visual representation of the statistical distribution.

15 Claims, 7 Drawing Sheets

(51) Int. Cl.
*A61B 5/04* (2006.01)
*A61B 5/0452* (2006.01)
*A61B 5/00* (2006.01)
*A61B 5/046* (2006.01)
*A61B 5/0464* (2006.01)
*A61B 18/14* (2006.01)
*A61B 18/00* (2006.01)

(52) U.S. Cl.
CPC .......... *A61B 5/0422* (2013.01); *A61B 5/0464* (2013.01); *A61B 5/04525* (2013.01); *A61B 5/6858* (2013.01); *A61B 5/743* (2013.01); *A61B 18/1492* (2013.01); *A61B 5/7264* (2013.01); *A61B 2018/00357* (2013.01); *A61B 2018/00577* (2013.01); *A61B 2018/00839* (2013.01); *A61B 2505/05* (2013.01)

(58) Field of Classification Search
CPC ... A61B 5/6859; A61B 5/743; A61B 18/1492; A61B 2018/00577
USPC ....................................................... 600/512
See application file for complete search history.

(56) References Cited

U.S. PATENT DOCUMENTS

| | | |
|---|---|---|
| 5,038,791 A | 8/1991 | Collins et al. |
| 5,158,092 A | 10/1992 | Glace |
| 5,254,088 A | 10/1993 | Lundquist et al. |
| 5,292,348 A | 3/1994 | Saumarez et al. |
| 5,433,198 A | 7/1995 | Desai |
| 5,485,849 A | 1/1996 | Panescu et al. |
| 5,582,609 A | 12/1996 | Swanson et al. |
| 5,598,848 A | 2/1997 | Swanson et al. |
| 5,647,870 A | 7/1997 | Kordis et al. |
| 5,657,755 A | 8/1997 | Desai |
| 5,810,740 A | 9/1998 | Paisner |
| 6,016,442 A | 1/2000 | Hsu et al. |
| 6,070,094 A | 5/2000 | Swanson et al. |
| 6,233,491 B1 | 5/2001 | Kordis et al. |
| 6,574,492 B1 | 6/2003 | Ben-Haim et al. |
| 6,600,948 B2 | 7/2003 | Ben-Haim et al. |
| 6,735,465 B2 | 5/2004 | Panescu |
| 6,950,689 B1 | 9/2005 | Willis et al. |
| 6,978,168 B2 | 12/2005 | Beatty et al. |
| 7,123,954 B2 | 10/2006 | Narayan et al. |
| 7,841,986 B2 | 11/2010 | He et al. |
| 9,144,391 B2 | 9/2015 | Thakur et al. |
| 9,332,920 B2 | 5/2016 | Thakur et al. |
| 9,579,034 B2 | 2/2017 | Thakur et al. |
| 2005/0007091 A1 | 1/2005 | Makeig et al. |
| 2005/0261599 A1 | 11/2005 | Shvilkin et al. |
| 2006/0074336 A1 | 4/2006 | Grieve et al. |
| 2006/0116594 A1 | 6/2006 | Zhang et al. |
| 2007/0299351 A1 | 12/2007 | Harlev et al. |
| 2008/0222109 A1 | 9/2008 | Sakurai |
| 2010/0298651 A1 | 11/2010 | Moon et al. |
| 2011/0251505 A1 | 10/2011 | Narayan et al. |
| 2012/0184858 A1 | 7/2012 | Harlev et al. |
| 2012/0296569 A1 | 11/2012 | Shahaf et al. |
| 2014/0336518 A1 | 11/2014 | Shuros et al. |
| 2014/0343388 A1 | 11/2014 | Thakur et al. |
| 2014/0343442 A1 | 11/2014 | Thakur et al. |
| 2014/0371616 A1 | 12/2014 | Narayan et al. |
| 2015/0065836 A1 | 3/2015 | Thakur et al. |
| 2015/0366476 A1 | 12/2015 | Laughner et al. |
| 2016/0073913 A1* | 3/2016 | Francis ................ A61B 5/6858 600/374 |
| 2016/0089050 A1 | 3/2016 | Thakur et al. |

FOREIGN PATENT DOCUMENTS

| | | |
|---|---|---|
| CN | 102245091 A | 11/2011 |
| CN | 105307558 A | 2/2016 |
| EP | 2996547 A1 | 3/2016 |
| GB | 1307211.1 * | 4/2013 ............. A61B 5/044 |
| JP | 2005131367 A | 5/2005 |
| JP | 4001959 B2 | 10/2007 |
| JP | 2007537823 A | 12/2007 |
| JP | 2009537252 A | 10/2009 |
| JP | 2012505047 A | 3/2012 |
| JP | 2013523345 A | 6/2013 |
| JP | 2014502556 A | 2/2014 |
| WO | WO0045700 A1 | 8/2000 |
| WO | 2006066324 A1 | 6/2006 |
| WO | 2011127211 A2 | 10/2011 |
| WO | 2012092016 A1 | 7/2012 |
| WO | 2012097059 A1 | 7/2012 |
| WO | 2012151008 A2 | 11/2012 |
| WO | 2013123549 A1 | 8/2013 |
| WO | 2014100464 A1 | 6/2014 |
| WO | 2014186684 A1 | 11/2014 |
| WO | 2015196107 A1 | 12/2015 |

OTHER PUBLICATIONS

Barbaro, V., et. al. Measure of Synchronisation of Right Atriai Depolarisation Wavefronts During Atrial Fibrillation. Med. Biol. Eng. Comput., 40(1): 56-62, 2002.

Brodda, K., et. al. A New Method for Detection of P Waves in Electrocardiograms. Signa Processing, 1(1): 15-25, 1979.

Holm, Magnus et al. A New Method for Analysis of Atrial Activation During Chronic Atrial Fibrillation in Man. IEEE Transactions on Biomedical Engineering, 43(2): 198-210, Feb. 1996.

International Search Report and Written Opinion issued in PCT/US2015/036746, mailed Sep. 1, 2015, 12 pages.

International Preliminary Report on Patentability issued in PCT/US2014/062876, mailed May 12, 2016, 9 pages.

Berkowitsch, Alexander et al., "Electrophysiological Heterogeneity of Atrial Fibrillation and Local Effect of Propafenone in the Human Right Atrium: Analysis Based on Symbolic dynamics", Journal of Interventional Cardiac Electrophysiology, Jun. 1, 2000, pp. 383-394.

Ciaccio, Edward J. et al., "Identification of recurring patterns in fractionated atrial electrograms using new transform coefficients", Biomedical engineering Online, vol. 11, No. 1, Jan. 1, 2012, 19 pages.

Fitzgerald, Tamara N. et all, "Identification of Cardiac Rhythm Features by Mathematical Analysis of Vector Fields", IEEE Transactions on Biomedical Engineering, vol. 52, No. 1, Jan. 2005, pp. 19-29.

Habel, N., et. al. The Temporal Variability of Dominant Frequency and Complex Fractionated Atrial Electrograms Constrains the Validity of Sequential Mapping in Human Atrial Fibrillation. Heart Rhythm, 7:586-593, 2010.

Houben, R. P. M., et. al. Processing of Intracardiac Electrograms in Atrial Fibrillation: Diagnosis of Electropathological Substrate of AF. IEEE Engineering in Medicine and Biology Magazine, 25(6):40-51, Nov. 1, 2006.

Houben, Richard P.M. et al., "Processing Intracardiac Electrograms in Atrial Fibrillation", Diagosis of Electropathologicai Substrate of AF, IEEE Engineering in Medicine and Biology Magazine, Nov./Dec. 2006, pp. 40-51.

International Preliminary Report on Patentability issued in PCT/US2013/076667, mailed Jul. 2, 2015, 9 pages.

International Preliminary Report on Patentabiiity issued in PCT/US2014/038357, mailed Nov. 26, 2015, 8 pages.

International Search Report and Written Opinion issued in PCT/US2014/038357, mailed Sep. 1, 2014, 11 pages.

International Search Report and Written Opinion issued in PCT/US2013/076667, mailed Mar. 20, 2014, 14 pages.

International Search Report and Written Opinion issued in PCT/US2014/062876, mailed Feb. 11, 2015, 12 pages.

International Search Report and Written Opinion] issued in PCT/US2014/053147, mailed Nov. 7, 2014, 12 pages.

Jadidi, A., et. al. Functional Nature of Electrograrn Fractionation Demonstrated by Left Atrial High-Density Mapping. Circ. Arrhythm Electrophysiol., 5:32-42, 2012.

(56) References Cited

OTHER PUBLICATIONS

Mabroukeh, Nzar R. et al., "A Taxonomy of Sequential Pattern Mining Algorithms", ACM Computng Suveys, vol. 43, No. 1, Nov. 1, 2010, pp. 1-41.
Masse, Stephane et al., "Wave similarity of human ventricular fibrillation from bipolar electrograms", Europace, vol. 9, No. 1, Jan. 1, 2007, 10 pages.
Rogers, Jack m et al., Recurrent Wavefront Morphologies: A Method for Quantifying the Complexity of Epicardial Activation Patterns, Annals of Biomedical Engineering, vol. 25, No. 5, 1997, pp. 761-768.
Sanders et al., "Spectral Analysis Identifies Sites of High-Frequency Activity Maintaining Atrial Fibrillation in Humans", Circulation, 112:789-797, 2005.
International Preliminary Report on Patentability issued in PCT/US2015/036746, issued on Dec. 20, 2016, 8 pages.
Masse, Stephane, et al. "Ventricular Fibrillation in Myopathic Human Hearts: Mechanistic Insights From in Vivo Global Endocardial and Epicardial Mapping." Am. J. Physiol. Heart Circ. Physiol. 292:H2589-H2597, 2007.

* cited by examiner

MEDICAL DEVICES FOR MAPPING CARDIAC TISSUE

CROSS-REFERENCE TO RELATED APPLICATION

This application claims priority to Provisional Application No. 62/015,007, filed Jun. 20, 2014, which is herein incorporated by reference in its entirety.

TECHNICAL FIELD

The present disclosure pertains to medical devices, and methods for manufacturing medical devices. More particularly, the present disclosure pertains to medical devices and methods for mapping and/or ablating cardiac tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

The invention provides design, material, manufacturing method, and use alternatives for medical devices. An example medical device includes a system for mapping the electrical activity of the heart. The system includes a catheter shaft with a plurality of electrodes. The system also includes a processor. The processor is capable of collecting a set of signals from at least one of the plurality of electrodes. The set of signals are collected over a time period. The processor is capable of calculating at least one propagation vector from the set of signals, generating a data set from the at least one propagation vector, generating a statistical distribution of the data set and generating a visual representation of the statistical distribution.

Alternatively or additionally to any of the examples above, in another example generating a statistical distribution of the data set includes generating a histogram of the data set.

Alternatively or additionally to any of the examples above, in another example generating a histogram of the data set includes generating a circular histogram.

Alternatively or additionally to any of the examples above, in another example, generating a visual representation of the statistical distribution includes displaying at least one circular histogram.

Alternatively or additionally to any of the examples above, in another example generating a visual representation of the statistical distribution includes performing an algorithmic computation of the data set.

Alternatively or additionally to any of the examples above, in another example the algorithmic computation of the data set generates a representative metric value for the data set.

Alternatively or additionally to any of the examples above, in another example the representative metric value is generated for each of the plurality of electrodes across the time period.

Alternatively or additionally to any of the examples above, another example includes displaying the representative metric values from each of the plurality of electrodes.

Alternatively or additionally to any of the examples above, another example includes one or more metric indicators and the metric indicators correspond to one or more representative metric values.

Alternatively or additionally to any of the examples above, in another example each metric indicator corresponds to a discrete metric interval and the discrete metric interval is a subdivision of an overall metric interval.

Alternatively or additionally to any of the examples above, another example includes creating a grid displaying the metric indicators for each of the plurality of electrodes.

Alternatively or additionally to any of the examples above, in another example performing an algorithmic computation of the data set includes determining the standard deviation, entropy, kurtosis, skewness and/or the circular average of the data set.

Alternatively or additionally to any of the examples above, in another example the at least one propagation vector includes a propagation angle and generating a data set includes defining the data set to include the vector angle for each of the set of signals from the at least one of the plurality of electrodes.

Alternatively or additionally to any of the examples above, in another example generating a visual representation of the statistical distribution includes displaying one or more of a histogram, a circular histogram, a two-dimensional grid, a three-dimensional model, a three-dimensional surface and a propagation vector.

Alternatively or additionally to any of the examples above, in another example generating a statistical distribution of the data set further comprises normalizing the data set.

Another example medical device includes a system for mapping the electrical activity of the heart. The system includes a catheter shaft with a plurality of electrodes. The system also includes a processor. The processor is capable of collecting a set of signals from at least one of the plurality of electrodes. The set of signal of signals are collected over a time period. The processor is also be capable of calculating at least one propagation vector from the set of signals, generating a data set from the at least one propagation vector, generating a statistical distribution of the data set and generating a visual representation of the statistical distribution.

Alternatively or additionally to any of the examples above, in another example generating a statistical distribution of the data set includes generating a histogram of the data set.

Alternatively or additionally to any of the examples above, in another example generating a histogram of the data set includes generating a circular histogram.

Alternatively or additionally to any of the examples above, in another example generating a visual representation of the statistical distribution includes displaying at least one circular histogram.

Alternatively or additionally to any of the examples above, in another example generating a visual representation of the statistical distribution includes performing an algorithmic computation of the data set.

Alternatively or additionally to any of the examples above, in another example the algorithmic computation of the data set generates a representative metric value for the data set.

Alternatively or additionally to any of the examples above, in another example the representative metric value is generated for each of the plurality of electrodes across the time period.

Alternatively or additionally to any of the examples above, another example includes displaying the representative metric values from each of the plurality of electrodes.

Alternatively or additionally to any of the examples above, another example includes one or more metric indicators and the metric indicators correspond to one or more representative metric values.

Alternatively or additionally to any of the examples above, in another example each metric indicator corresponds to a discrete metric interval, wherein the discrete metric interval is a subdivision of an overall metric interval.

Alternatively or additionally to any of the examples above, another example includes creating a grid displaying the metric indicators for each of the plurality of electrodes.

Alternatively or additionally to any of the examples above, in another example performing an algorithmic computation of the data set includes determining the standard deviation, entropy, kurtosis, skewness and/or the circular average of the data set.

Alternatively or additionally to any of the examples above, in another example the at least one propagation vector includes a propagation angle and generating a data set includes defining the data set to include the vector angle for each of the set of signals from the at least one of the plurality of electrodes.

Alternatively or additionally to any of the examples above, in another example generating a visual representation of the statistical distribution includes displaying one or more of a histogram, a circular histogram, a two-dimensional grid, a three-dimensional model, a three-dimensional surface and a propagation vector.

Another example medical device includes a method for mapping the electrical activity of the heart. The method includes sensing a plurality of signals with a plurality of electrodes positioned within the heart over a time period, determining a direction of at least one of the plurality of signals and generating a data set. The data set includes at least one vector angle. The method also includes generating a diagnostic image from the at least one of the plurality of electrodes. Additionally, generating the diagnostic image utilizes the data set.

Alternatively or additionally to any of the examples above, in another example generating the data set further includes generating a histogram.

Alternatively or additionally to any of the examples above, in another example generating the data set further includes performing a statistical analysis on at least one vector angle.

Alternatively or additionally to any of the examples above, in another example the histogram is a circular histogram. Additionally, generating the diagnostic image includes calculating a standard deviation, entropy, kurtosis, skewness and/or the circular average of the data set.

Alternatively or additionally to any of the examples above, in another example generating the data set further includes generating at least one representative metric and the at least one representative metric correlates to at least one vector angle.

Alternatively or additionally to any of the examples above, in another example generating a diagnostic image includes a visual representation and the visual representation includes displaying one or more of a histogram, a circular histogram, a two-dimensional grid, a three-dimensional model, a three-dimensional surface and a propagation vector.

Another example medical device includes a system for mapping the electrical activity of the heart. The system includes a catheter shaft with a plurality of electrodes. The system also includes a processor. The processor is capable of collecting a set of signals from at least one of the plurality of electrodes. The set of signals are collected over a time period. The system includes determining an activation time for at least one of the plurality of electrodes and calculating a propagation vector. The propagation vector includes a vector angle for the at least one of the plurality of electrodes. Calculating the propagation vector utilizes an activation time from at least one of the plurality of electrodes. The system also includes generating a data set from the at least one of the plurality of electrodes. The data set includes at least one vector angle. The system also includes generating a statistical distribution of the data set and generating a visual representation of the shape of the statistical distribution.

Another example medical device includes a method for mapping the electrical activity of the heart. The method includes advancing a catheter to a target region within a cardiac chamber. The catheter includes a catheter shaft with a plurality of electrodes and a processor coupled to the catheter shaft. The method also includes collecting a set of signals from at least one of the plurality of electrodes. The set of signal of signals are collected over a time period. The method also includes calculating at least one propagation vector from the set of signals, generating a data set from the at least one propagation vector, generating a statistical distribution of the data set and displaying a visual representation of the statistical distribution. Displaying a visual representation includes displaying one or more of a confidence level, reliability level and stability level.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
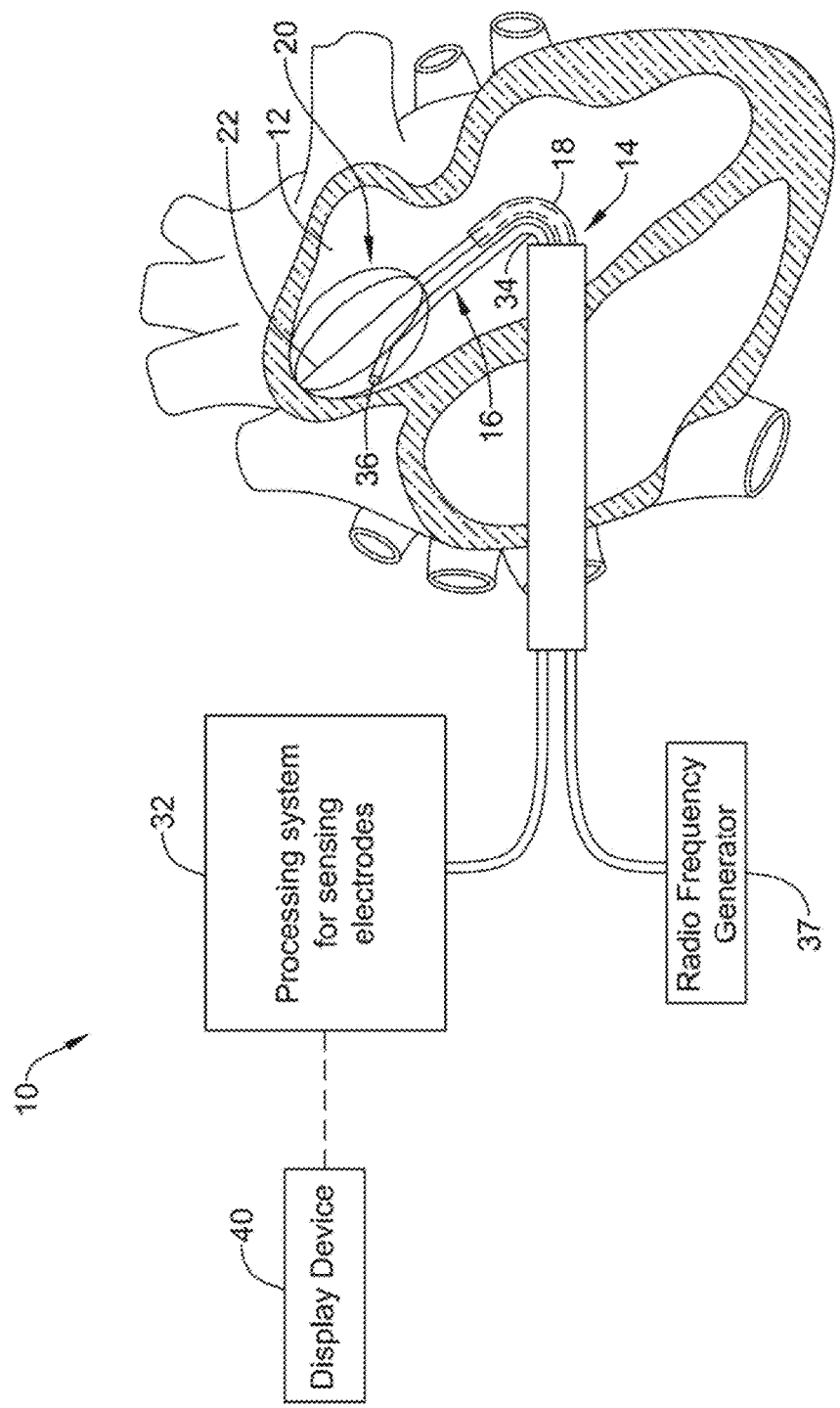
FIG. 1 is a schematic view of an example catheter system for accessing a targeted tissue region in the body for diagnostic and therapeutic purposes.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a constellation catheter or other mapping/sensing device having a plurality of sensors into a cardiac chamber. The sensors detect the electric activity of the heart at sensor locations. It may be desirable to have the electric activity processed into electrogram signals that accurately represent cellular excitation through cardiac tissue relative to the sensor locations. A processing system may then analyze and output the signal to a display device. Further, the processing system may output the signal as an activation map. The physician may use the activation map to perform a diagnostic procedure.

However, in some cases the sensing electrodes may fail to accurately detect the electrical activity of heart. The failure of the electrodes to detect a signal may limit and/or reduce the ability of the processing system to accurately display information used for diagnostic procedures. For example, an activation map may be generated that contains missing information and/or inaccurate visual representations. Therefore, it may be desirable to replace poor or non-existent electrical signal information with information that is believed to be accurate. In some instances, interpolation may be used to replace poor/missing data. Standard interpolation methods may have limitations due to both the temporal nature of the activation signals and the three-dimensional spatial configuration of sensing electrodes located in an anatomical region. The methods and systems disclosed herein are designed to overcome at least some of the limitations of standard interpolation methods used to interpolate poor or non-existent activation signals. For example, some of the methods disclosed herein may utilize data reduction processes in order to simplify activation maps or otherwise replace/fill in poor or non-existent data. Other methods and medical devices are also disclosed.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, nerves, blood vessels and other regions of the body, including in systems that are not necessarily catheter-based. It is contemplated that that system 10 may perform procedures alone or in combination with other applications and/or procedures. For example, in addition to performing ablation procedures, system 10 may be utilized to map the electrical activity of the heart. Further, mapping the electrical activity of the heart may be performed alone or in conjunction with an ablation procedure.

The system 10 includes a mapping probe 14 and an ablation probe 16. Each probe 14/16 may be separately introduced into the selected heart region 12 through a vein or artery (e.g., the femoral vein or artery) using a suitable percutaneous access technique. Alternatively, the mapping probe 14 and ablation probe 16 can be assembled in an integrated structure for simultaneous introduction and deployment in the heart region 12.

The mapping probe 14 may have a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used. The multiple electrode structure 20 carries a plurality of mapping electrodes 24 (not explicitly shown on FIG. 1, but shown on FIG. 2) each having an electrode location on structure 20 and a conductive member. Each electrode 24 may be configured to sense intrinsic physiological activity in the anatomical region. In some embodiments, the electrodes 24 may be configured to detect activation signals of the intrinsic physiological activity within the anatomical structure (e.g., the activation times of cardiac activity).

The electrodes 24 are electrically coupled to a processing system 32. A signal wire (not shown) may be electrically coupled to each electrode 24 on the basket structure 20. The wires may extend through the body 18 of the probe 14 and electrically couple each electrode 24 to an input of the processing system 32. The electrodes 24 sense electrical activity in the anatomical region, e.g., myocardial tissue. The sensed activity (e.g., activation signals) may be processed by the processing system 32 to assist the physician by generating an anatomical map (e.g., a vector field map) to identify the site or sites within the heart appropriate for a diagnostic and/or treatment procedure, e.g. an ablation procedure. For example, the processing system 32 may identify a near-field signal component (e.g., activation signals originating from cellular tissue adjacent to the mapping electrode 24) or from an obstructive far-field signal component (e.g., activation signals originating from non-adjacent tissue). For example, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

The processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the electrical activity in the myocardial tissue adjacent to the electrodes 24. For example, in some embodiments, the processing system 32 is configured to detect electrical activity associated with a dominant rotor or divergent activation pattern in the anatomical feature being mapped. For example, dominant rotors and/or divergent activation patterns may have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristic, such as an isochronal map, activation time map, action potential duration (APD) map, a vector field map, a contour map, a reliability map, an electrogram, a cardiac action potential and the like. The relevant characteristics may be used by the physician to identify a site suitable for ablation therapy.

The ablation probe 16 includes a flexible catheter body 34 that carries one or more ablation electrodes 36. The one or more ablation electrodes 36 are electrically connected to a radio frequency (RF) generator 37 that is configured to deliver ablation energy to the one or more ablation electrodes 36. The ablation probe 16 may be movable with respect to the anatomical feature to be treated, as well as the structure 20. The ablation probe 16 may be positionable between or adjacent to electrodes 24 of the structure 20 as the one or more ablation electrodes 36 are positioned with respect to the tissue to be treated.

The processing system 32 may output data to a suitable output or display device 40, which may display relevant information for a clinician. In the illustrated embodiment, device 40 is a CRT, LED, or other type of display, or a printer. Device 40 presents the relevant characteristics in a format most useful to the physician. In addition, processing system 32 may generate position-identifying output for display on device 40 that aids the physician in guiding ablation electrode(s) 36 into contact with tissue at the site identified for ablation.

Figure 2:
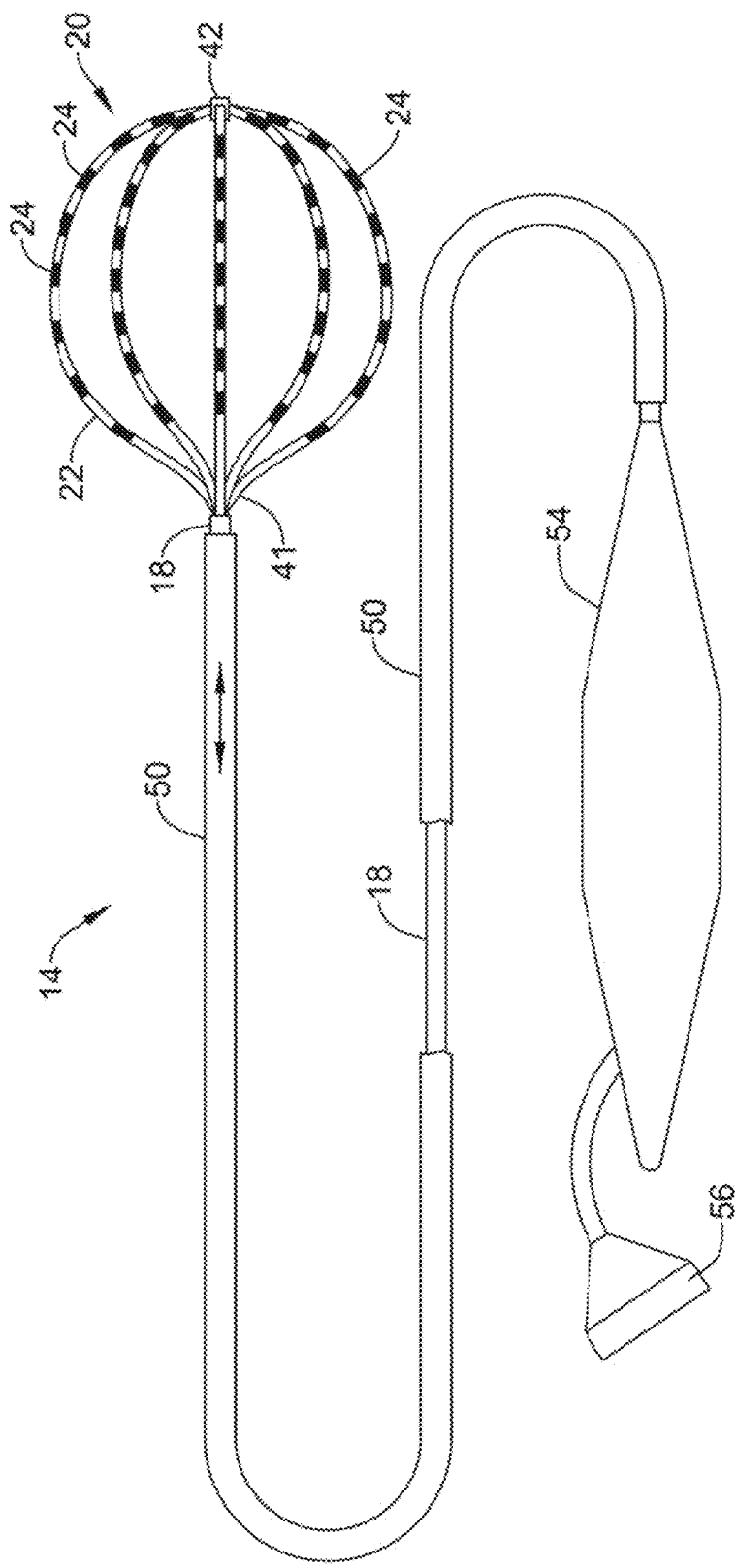
FIG. 2 is a schematic view of an example mapping catheter having a basket functional element carrying structure for use in association with the system of FIG. 1.

FIG. 2 illustrates mapping catheter 14 and shows electrodes 24 at the distal end suitable for use in the system 10 shown in FIG. 1. Mapping catheter 14 may have a flexible catheter body 18, the distal end of which may carry three dimensional structure 20 with mapping electrodes or sensors 24. Mapping electrodes 24 may sense electrical activity (e.g., activation signals) in the myocardial tissue. The sensed activity may be processed by the processing system 32 to assist the physician in identifying the site or sites having a heart rhythm disorder or other myocardial pathology via generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed herein, the three dimensional structure 20 may take the form of a basket defining an open interior space 22. In some embodiments, the splines 44 are made of a resilient inert material, such as Nitinol, other metals, silicone rubber, suitable polymers, or the like and are connected between the base member 41 and the end cap 42 in a resilient, pretensioned condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 may be movable along the major axis of the catheter body 18. Moving the sheath 50 distally relative to catheter body 18 may cause sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 proximally relative to the catheter body may expose the three dimensional structure 20, allowing the structure 20 to elastically expand and assume the pretensed position illustrated in FIG. 2.

A signal wire (not shown) may be electrically coupled to each mapping electrode 24. The wires may extend through the body 18 of the mapping catheter 20 (or otherwise through and/or along the body 18) into a handle 54, in which they are coupled to an external connector 56, which may be a multiple pin connector. The connector 56 electrically couples the mapping electrodes 24 to the processing system 32. These are just examples. Some addition details regarding these and other example mapping systems and methods for processing signals generated by the mapping catheter can be found in U.S. Pat. Nos. 6,070,094, 6,233,491, and 6,735,465, the disclosures of which are hereby expressly incorporated herein by reference.

Figure 3:
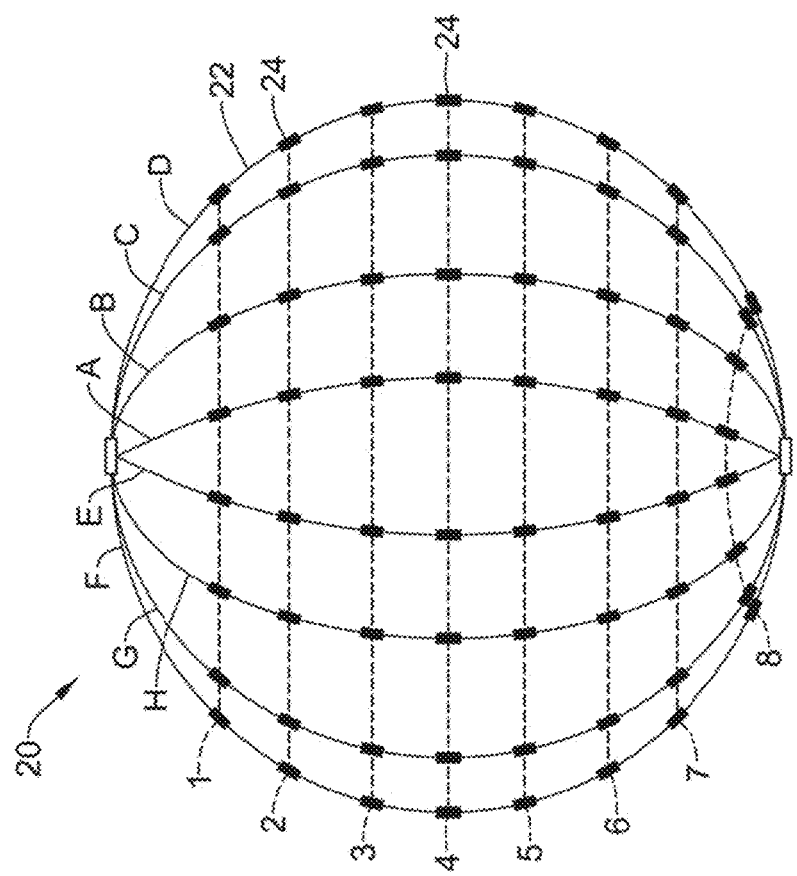
FIG. 3 is a schematic view of an example functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g. left atrium, left ventricle, right atrium, or right ventricle of the heart), the processing system 32 is configured to record the activation signals from each electrode 24 channel related to physiological activity of the anatomical structure (e.g., the electrodes 24 measure electrical activation signals associated with the physiology of the anatomical structure). The activation signals of physiological activity may be sensed in response to intrinsic physiological activity or based on a predetermined pacing protocol instituted by at least one of the plurality of electrodes 24.

Basket structure 20 may vary in size from a small basket (capable of mapping a small, localized section of the cardiac chamber) to a large basket (capable of mapping a majority of a cardiac chamber). Utilizing a small basket structure may result in processing system 32 having to combine localized recordings together. Localized recordings may overlap one another, and therefore, to achieve a "global" representation of the cardiac chamber, it may be necessary to combine, or "stitch," local recordings together. Methodologies for stitching localized recordings are disclosed in U.S. Patent Application No. 61/898,312 entitled "Medical Device for High Resolution Mapping Using Localized Matching", the entire disclosure of which is fully incorporated by reference.

The arrangement, size, spacing and location of electrodes along a constellation catheter or other mapping/sensing device, in combination with the specific geometry of the targeted anatomical structure, may contribute to the ability (or inability) of electrodes 24 to sense, measure, collect and transmit electrical activity of cellular tissue. As stated, because splines 44 of a mapping catheter, constellation catheter or other similar sensing device are bendable, they may conform to a specific anatomical region in a variety of shapes and/or configurations. Further, at any given position in the anatomical region, the electrode basket structure 20 may be manipulated such that one or more splines 44 may not contact adjacent physiological tissue. For example, splines 44 may twist, bend or lie atop one another, thereby separating splines 44 from nearby physiological tissue. Additionally, because electrodes 24 are disposed on one or more of splines 44, they also may not maintain contact with adjacent physiological tissue.

In addition to that stated above, electrodes 24 may not be in contact with adjacent physiological tissue for other reasons. For example, manipulation of mapping catheter 14 may result in movement of electrodes 24, thereby creating poor electrode-to-tissue contact. Further, electrodes 24 may be positioned adjacent fibrous, dead or functionally refractory tissue. Electrodes 24 positioned adjacent fibrous, dead or functionally refractory tissue may not be able to sense changes in electrical potential because fibrous, dead or functionally refractory tissue may be incapable of depolarizing and/or responding to changes in electrical potential. Finally, far-field ventricular events and electrical line noise may distort measurement of tissue activity.

However, electrodes 24 that contact healthy, responsive cellular tissue may sense a change in the voltage potential of a propagating cellular activation wavefront. The change in voltage potential of a cellular tissue may be sensed, collected and displayed as an electrogram. An electrogram may be a visual representation of the change in voltage potential of the cellular tissue over time. Additionally, it may be desirable to define a specific characteristic of an electrogram as a "fiducial" point of the electrical signal. For purposes of this disclosure, a fiducial point may be understood as a characteristic of an electrogram that can be utilized as an identifying characteristic of cellular activation. Fiducial points may correspond to the peak amplitude, change in slope, and/or deflection of the electrical signal. It is contemplated that fiducial points may include other characteristics of an electrogram. Further, fiducial points may be identified manually by a clinician and/or automatically by processing system 32.

An electrogram representing a change in voltage potential over time may be defined as visually displaying the electrical signal in the "time domain." However, it is generally understood that any electrical signal has a corollary representation in the frequency domain. Transforms (e.g. Fourier) may be utilized to transform signals between the time domain and frequency domain, as desired. It is contemplated that at least some embodiments disclosed herein may be equally applied to signals in both the time and frequency domain. Further, it is contemplated that at least some embodiments disclosed herein may be equally applied to the derivatives of any signal, in both the time and frequency domain. Additionally, it is contemplated that at least some embodiments disclosed herein may be equally applied to the transform (e.g., Hilbert, etc.) of any signal in both the time and frequency domain.

As suggested herein, fiducial points may be used to identify the "activation," or firing, of cellular tissue. For example, processing system 32 may determine the "activation time" of cellular firing by comparing the fiducial point to a reference time point. The reference time point may include the time at which a cellular activation wavefront passes a reference electrode. Alternatively, processing system 32 may determine activation times by analyzing the dominant frequency of the cardiac electrical activity and comparing frequency-domain signal characteristics to time-domain signal characteristics. Methodologies for using a the dominant frequency to select activation times are disclosed in U.S. Patent Application No. 61/991,235 entitled "Medical Devices for Mapping Cardiac Tissue", the entire disclosure of which is fully incorporated by reference. It is understood that processing system 32 may identify the activation times of multiple electrodes 24 as a cellular activation wavefront moves underneath multiple electrodes 24 by applying the methodologies described above to multiple electrodes 24.

The selected time interval over which electrical activity is analyzed may span one or more heart cycles or "beats." During atrial fibrillation, for example, the number of cardiac cycles analyzed over a selected time period may be 20, 50, 100, 200 or 300 beats. Further, processing system 32 may "collect" data (including cellular activation times) relating to cardiac electrical activity spanning several cardiac beats in a selected time frame for one or more of electrodes 24. In some embodiments, a sampling time frame may be 30-40 seconds, during which time processing system 32 may collect electrical activity data from 30-300 cardiac cycles.

In some instances, processing system 32 may determine propagation vectors. Propagation vectors may be generated through one or more different methodologies.

For example, once processing system 32 has collected activation times for one or more of electrodes 24, processing system may determine a propagation vector (including a magnitude and angle) for each activation time collected from one or more of electrodes 24 spanning the sampled time interval. For example, during atrial fibrillation, a given electrode 24 may collect 200-300 activation times during a given sampling period (e.g. 30-40 sec), and consequently, processing system 32 may be able to determine 200-300 propagation vectors (including a magnitude and angle) corresponding to the 200-300 beats. As stated, the propagation vector may include a magnitude and direction of cellular wavefront propagation. It is contemplated that the magnitude of the propagation vector may represent velocity, inverse velocity, confidence, or other relevant measures. The magnitude may also be set to a fixed value. Additionally, the direction (e.g. propagation angle) and velocity of cellular wavefront propagation may be determined by a comparing the activation times sensed by neighboring electrodes to the target electrode for which the propagation vector is being determined. For example, processing system 32 may utilize circular averaging to determine the vector propagation angle. Methodologies for determining propagation vectors and a local direction of propagation are disclosed in U.S. Patent Application No. 61/823,386 entitled "Representation and Identification of Activity Patterns during Electro-physiology Mapping Using Vector Fields," the entire disclosure of which is fully incorporated by reference.

In another example, propagation vectors may be determined without explicitly determining activation times. For example, propagation vectors may be determined manually, statistically and/or through the processing of orthogonally placed bipoles. These are just examples. Other methods independent of determining activation times are contemplated. Vectors derived from these methods may be processed in a manner similar to vectors derived from activation times.

In addition to at least some of the embodiments described above, processing system 32 may generate a data set from the propagation vectors (including a magnitude and angle) collected from a given electrode 24. Further, processing system 32 may generate a unique data set for each of electrodes 24 on electrode structure 20. In some instances, the data set may include propagation vectors for each cardiac beat over a given sampling period. Additionally, the data set may include vector angles, vector magnitude, combinations thereof, or the like.

For example, the data set may include propagation angles collected for each cardiac beat over a given sampling period. A single propagation angle may indicate the direction of wavefront propagation for a single cardiac beat at a specific electrode location. Further, processing system 32 may generate a data set using different propagation angles acquired during the sampling period. For example, when the sampling period includes 200-300 activation times, the corresponding data set may include 200-300 corresponding propagation angles.

Additionally, the data set may include the magnitude of the wavefront propagation for a single cardiac beat at a specific electrode location. For example, the data set may include a vector magnitude collected for each cardiac beat over a given sampling period. The magnitude may correspond to the velocity, inverse velocity, confidence, or other relevant measures of the wavefront propagation.

Having generated a data set for one or more of electrodes 24, processing system 32 may generate a statistical distribution of one or more data sets. For example, processing system 32 may generate a histogram of a data set. A histogram is one example of a statistical methodology for analyzing a given set of data. Other statistical methodologies are contemplated. In practice, processing system 32 may be configured to analyze and compute sensed data such as a histogram or visual representation. The actual data may or may not be output and/or displayed. Processing system 32 may utilize the Freedman-Diaconis rule to create discrete equal time intervals based on the characteristics inherent to a given data set. It is contemplated the other statistical rules may be utilized to create a statistical distribution of the data set. Further, it is contemplated that in some embodiments the processing system may create statistical distributions that differ visually from one another.

Figure 4:
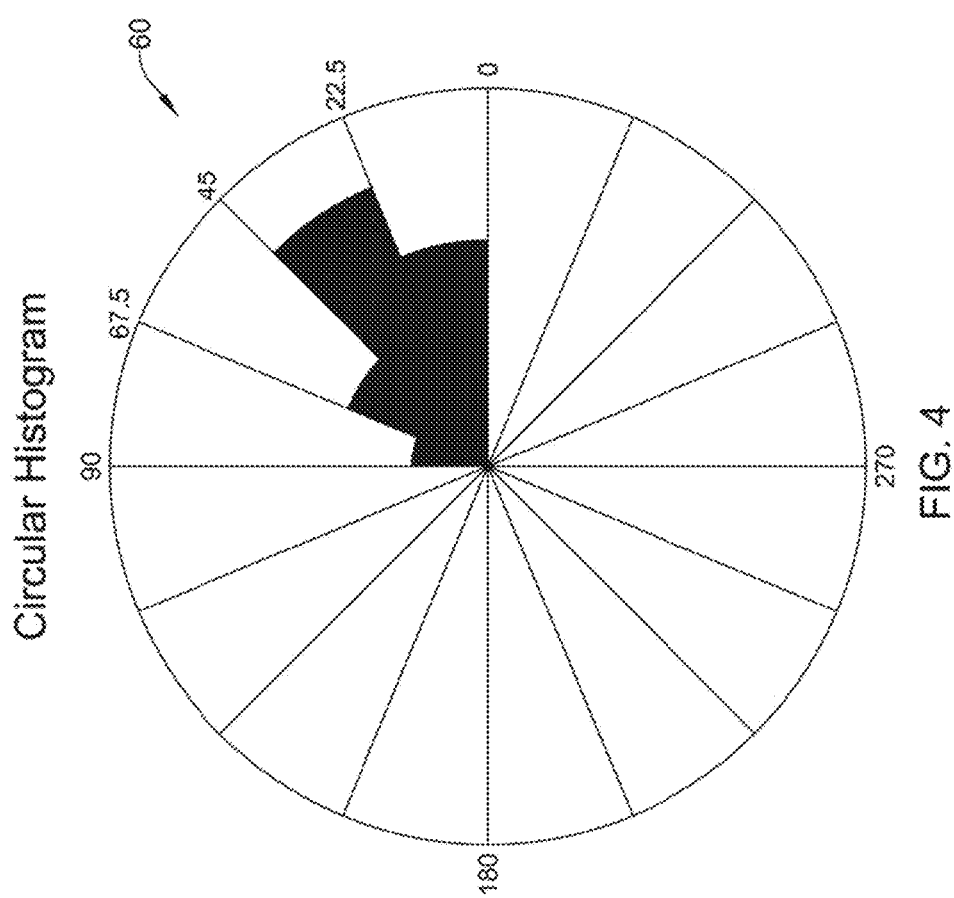
FIG. 4 illustrates an example circular histogram.

In some instances, processing system 32 may generate a circular histogram corresponding to a given data set. FIG. 4 illustrates an example circular histogram 60. A circular histogram may graphically illustrate the distribution of a data set. Further, a circular histogram may be particularly useful in displaying the distribution of data corresponding to angular measurements. For example, a circular histogram may be useful to display distribution data relating to propagation angles for propagation vectors. For illustrative purposes, circular histogram 60 illustrates the frequency for which given data points (e.g. propagation angles, magnitude, etc.) occur within a given data set. Circular histogram 60 may be divided into multiple frequency ranges. For example, FIG. 4 is divided into four segments: 0-22.5 degrees, 22.6-45 degrees, 45.1-67.5 degrees, and 67.6-90 degrees. The magnitude and/or sum of the occurrences of data points is identified by the size and/or "height" of the bars in pre-determined frequency ranges. For example, in FIG. 4, the frequency range displaying the most propagation angles is 22.6-45 degrees. The frequency range displaying the fewest propagation angles is 67.6-90 degrees.

While FIG. 4 displays a circular histogram, it is contemplated that the embodiments disclosed herein may utilize and/or include other histograms and/or other graphical representations of a data set. Further, processing system 32 may not generate a visual representation of a data set to generate a statistical representation. Rather, processing system 32 may generate a statistical distribution independent of generating a graphical representation of the data set. Further, it is understood that processing system may manipulate and/or tailor the data set to fit the statistical representation. For example, processing system 32 may normalize that data prior, during or after generation of the histogram. Normalization is one example data manipulation technique. Other techniques are contemplated.

In addition, it may be desirable to compare the statistical distributions between the plurality of electrodes 24. Further, it may be desirable to characterize the shape of the statistical distribution. For example, processing system may characterize the shape of a statistical distribution by performing an algorithmic computation on the distribution. It is contemplated that performing an algorithmic computation on a statistical distribution may include performing the algorithm computation on the data set used to generate the statistical distribution.

To characterize the statistical distribution and/or the shape of the distribution, processing system 32 may utilize one of several algorithmic computations. For example, processing system 32 may calculate the standard deviation, entropy, kurtosis, skewness and/or the circular average of the data set and/or graphical representation of the data set. Further, the algorithmic computation may generate a representative metric value for the data set and/or graphical representation. The representative metric value may be the value output by the algorithmic computation generated for a given data set and/or graphical representation. For example, the standard deviation value calculated for a given data set may be considered a representative metric value for that data set and/or graphical representation. Therefore, for a given sampling period, processing system 32 may generate a representative metric value for one or more of the plurality of electrodes 24. For example, processing system may generate 64 individual representative metric values.

As stated above, processing system 32 may not need to generate a visual representation of a data set to characterize the shape of a data set and/or graphical representation. Rather, processing system 32 may characterize the shape of a data set and/or graphical representation independent of generating a graphical representation of the data set. Further, it is understood that processing system may manipulate and/or tailor the data set to fit the statistical representation. For example, processing system 32 may normalize that data prior, during or after generation of the histogram. Normalization is an example data manipulation technique, however, other techniques are contemplated.

In some embodiments, it may be desirable to compare and contrast the representative metric values across a given data set and/or graphical representation generated for one or more of the plurality of electrodes 24 across a given sampling period. To better compare and/or contrast representative metric values, it may be desirable to correlate representative metric values to a metric indicator. Metric indicators may include one or more representative number, color, texture, shape or other visual indicators that can be easily visualized on a display.

Similarly to the methodology discussed above in relation to histogram generation, representative metric values generated for the plurality of electrodes 24 may be sorted and/or "binned" to aid comparison among values. For example, one methodology may include ranking the data from the lowest value to the greatest value and sub-dividing the data into discrete metric intervals based on the difference between the greatest value and lowest value. The representative metric values may be sorted or "binned" into the different metric intervals. Each metric interval may correspond to a discrete range of the overall data set.

Figure 5:
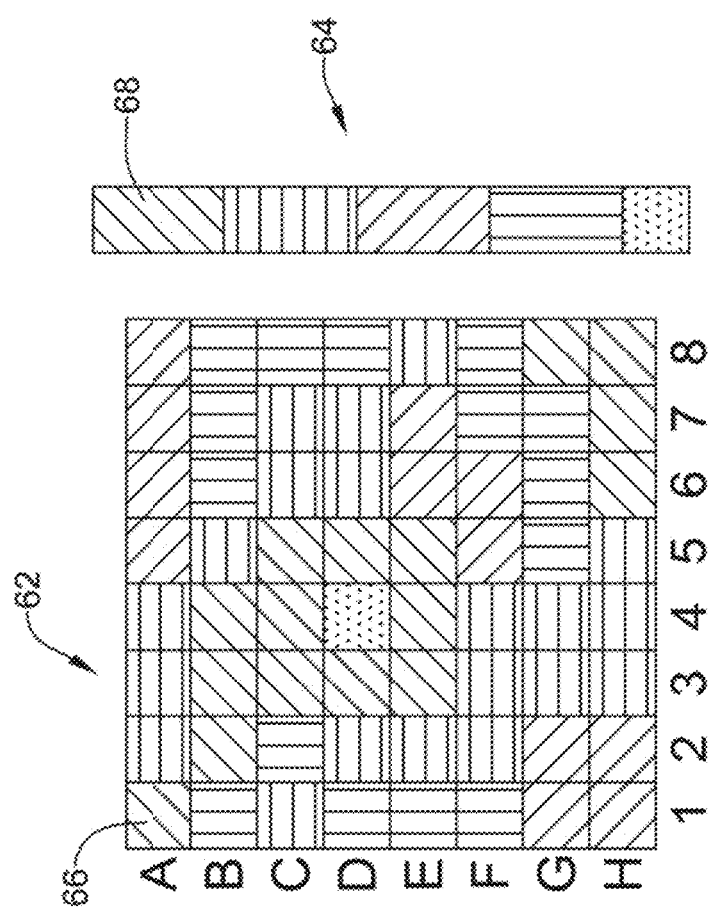
FIG. 5 illustrates an example grid displaying representative metric values.

FIG. 5 shows a key 64 for correlating the metric intervals with each of the electrode 24 locations on a grid 62. In this example, key 64 displays five discrete metric intervals corresponding to the "bins" into which the representative metric values may be sorted and/or assigned. Further, each metric interval includes a specific metric indicator. For example, electrode location 66 displays a metric indicator of "diagonal lines." The representative value of location 66 corresponds to the representative value range of metric interval 68.

Figure 6:
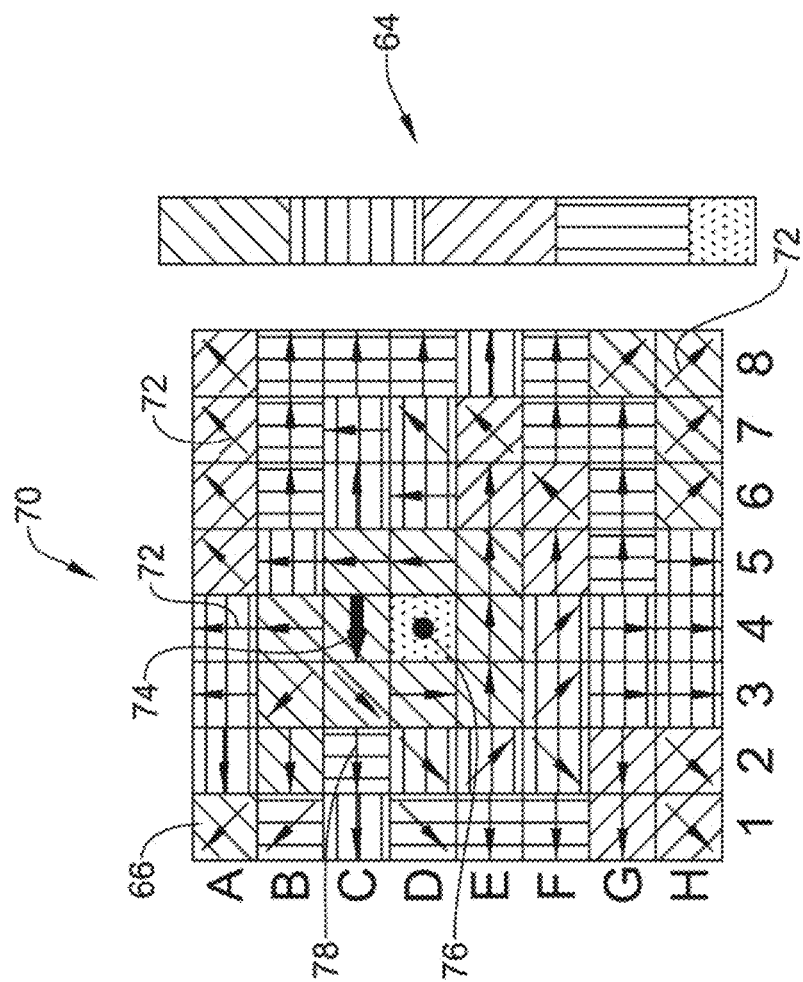
FIG. 6 illustrates an example grid displaying representative metric values including propagation vectors.

It is contemplated that a variety of color, texture, number, shape and/or other visual indicator combinations may be included in generating grid 62. Further, in at least some embodiments, grid 62 may display one or more metric indicators concurrently. For example, it may be desirable to display a metric indicator corresponding to a representative metric value along with a propagation vector indicating the direction and/or magnitude of cellular wavefront propagation. FIG. 6 illustrates grid 70 displaying both metric indicators (as described above) in addition to propagation vectors 72 indicating the direction of wavefront propagation for each electrode location. It is contemplated that wavefront propagation vectors 72 may be generated using one of several methodologies. For example, wavefront propagation vectors 72 may be determined by calculating the mean value for both the direction and magnitude for each propagation vector collected across a sampling time period.

As stated above, within a given sampling time period, processing system 32 may determine a propagation vector (including a magnitude and angle) for each beat occurring in the time period. Therefore, a propagation vector 72 displayed in example grid 70 may reflect the mean value of the magnitude and angle for all propagation vectors determined during a given time period. In other words, propagation vectors 72 may be determined by performing a statistical computation on the data set of propagation vectors and angles collected for each electrode location. In some embodiments, the statistical computation may be the mean, however, other computations are contemplated. For example, the propagation vectors may represent the median, mode or any other computation (statistical or otherwise).

In addition to the above, it is contemplated that the shape, size, color or other attribute of propagation arrow 72 may convey information related to sensed and collected cardiac electrical information. For example, propagation arrow 74 may display a "thickness" that is greater than propagation arrow 78. The thickness of the arrow may indicate a greater confidence in the propagation angle for that particular electrode location. It is contemplated that the shape attributes of a given propagation arrow may convey diagnostic information other than the confidence and/or reliability of the propagation angle. For example, the propagation angle may convey information about magnitude or other diagnostic information.

In addition, display 70 may convey diagnostic or electrical information by displaying symbols in addition to and/or different from an arrow shape. For example electrode location D4 in FIG. 6 displays a center dot 76. Center dot 76 may correspond to an inconclusive and/or randomness associated with the computation of a propagation angle for that particular electrode location. In some embodiments, a center dot may correspond to the center or core of a rotor pattern. It should be understood that the above description is merely illustrative of one possible display configuration. Other symbols, shapes, indicators and combinations are contemplated.

In other instances, display 70 may convey information corresponding to a range of electrical signal velocities and/or other characteristics of cardiac signal propagation. For example, display 70 may display slow conduction areas, fast conduction areas, and/or a range of velocity conduction from slow conduction areas to fast conduction areas. For example, the stimulation (e.g. via external pacing, native AF rate, etc.) rate may impact the velocity. This may allow the health of the tissue to be estimated. For example, the health of the tissue may be correlated to the velocity range. Therefore, in some instances it may be beneficial to display a range of velocities on display 70. It is contemplated that signal velocity may be displayed using any of the methodologies disclosed above relating to the use of visual indicators and/or shapes.

Figure 7:
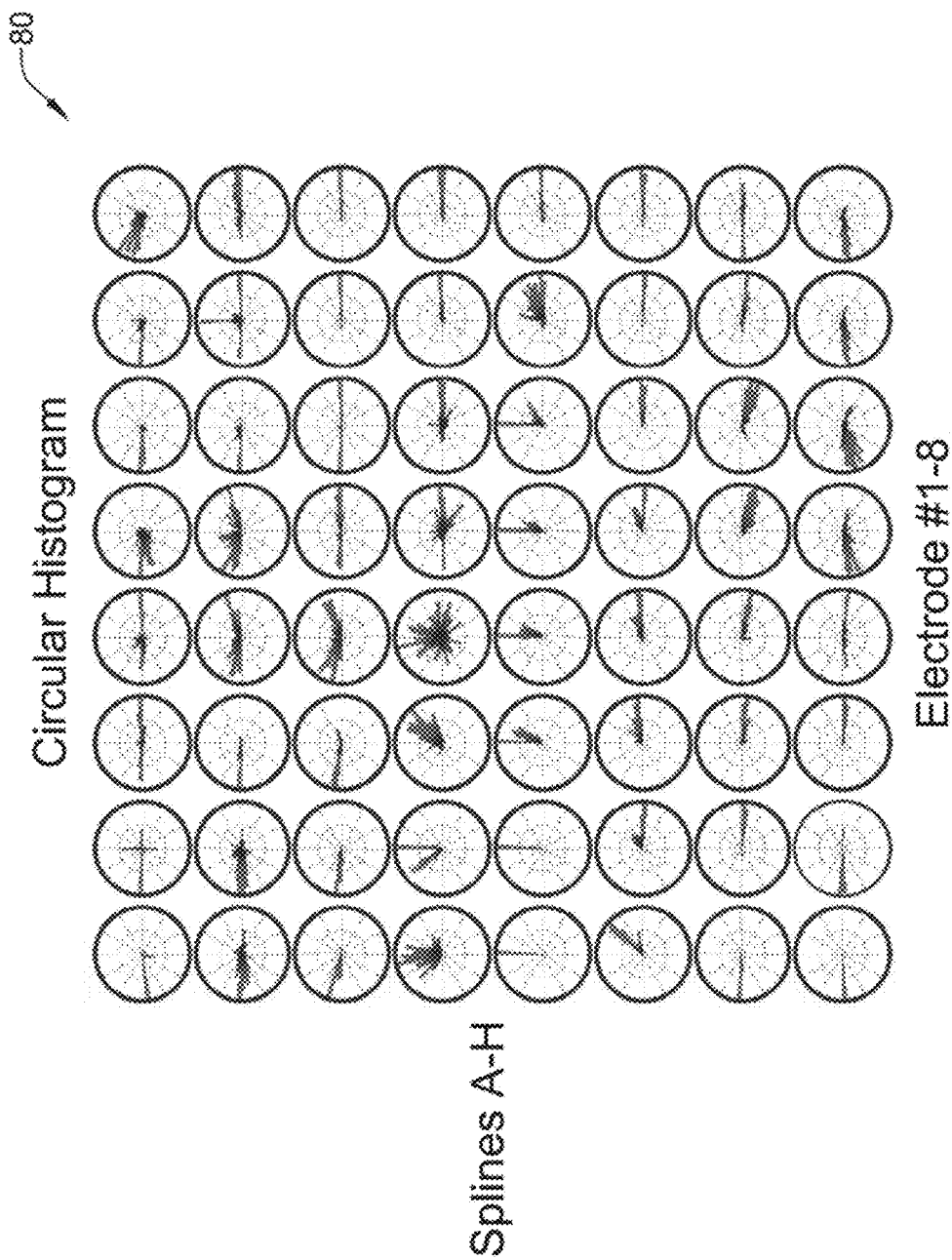
FIG. 7 illustrates an example two-dimensional matrix of circular histograms corresponding to particular electrode locations.

In addition to a grid, processing system 32 may generate other visual representations of the shape of a statistical distribution. For example, FIG. 7 displays an 8×8 matrix 80 of circular histograms corresponding to the data sets for each of the 64 electrodes 24 on electrode structure 20. As stated above, each individual circular histogram may be generated from a data set collected across multiple beats of a sampling time period. Further, the collected data may represent propagation vectors and/or propagation angles of a propagating cellular activation wavefront. FIG. 7 displays circular histograms in an 8×8 matrix, however, it is contemplated that a matrix of other dimensions may be generated. The size of the matrix may correspond to the number of electrodes 24 used to map the electrical activity. For example, matrices sized 2×2, 4×4, 4×6, 3×5, 6×6, or combinations thereof are contemplated.

It is contemplated that grid 62 and/or any other matrix, collection or data representations disclosed herein may be displayed on a display. The display may include three-dimensional representations and/or visualizations. For example, the display may include a sphere and/or cylinder, anatomical shell, surface and/or topographical visualization that represents the spatial relationships among the electrodes or between the catheter and the anatomy. Additionally, grid 62 and/or any other matrix, collection or data representations may help a clinician identify the direction of propagation of cellular firing. In at least some embodiments, the patterned/textured grid 62 and metric interval 64 may both be shown on a display.

As stated above, in a normal functioning heart, electrical discharge of the myocardial cells may occur in a systematic, linear fashion. Therefore, detection of non-linear propagation of the cellular excitation wavefront may be indicative of cellular firing in an abnormal fashion. For example, cellular firing in a rotating pattern may indicate the presence of dominant rotors and/or divergent activation patterns. Further, because the presence of the abnormal cellular firing may occur over localized target tissue regions, it is possible that electrical activity may change form, strength or direction when propagating around, within, among or adjacent to diseased or abnormal cellular tissue. Identification of these localized areas of diseased or abnormal tissue may provide a clinician with a location for which to perform a diagnostic procedure. For example, identification of an area consisting of reentrant or rotor circuits may be indicative of an area of diseased or abnormal cellular tissue. The diseased or abnormal cellular tissue may then be targeted for an ablative procedure.

To that end, grid 62 may be used to identify areas of circular, adherent, rotor or other abnormal cellular excitation wavefront propagation. Further, it is contemplated that processing system 32 may include one or more "rules" for identifying diagnostically relevant patterns, correlations, fittings, matching, templates, or the like within the data set, data characterization and/or visual representation. For example, processing system 32 may include rules that identify the core of a rotor pattern. The core of a rotor pattern may include a data set and/or shape characterized as having a threshold "randomness" or "uncertainty" level. In other words, processing system 32 may be able to identify that the propagation vector, angle and/or electrical activity corresponding to a given electrode location may not repeat in a consistent manner over a sampling time period. Further, processing system may further include a rule that identifies a rotor by identifying a rotor core location surrounded by propagation vectors which include consistent propagation angles over the sampling period. Upon identification of a rotor core and/or rotor, processing system 32 may output a visual indicator corresponding to the rotor and/or core. The visual indicator may include an arrow on a display, text, color, highlighting or the like.

Another rule contemplated herein may include the identification of two or more underlying dominant electrical activation cycles occurring at two or more frequencies across two or more different groups of electrodes 24. During an adverse cardiac event (e.g. atrial fibrillation), the electrical activity may present as a "bimodal" distribution. For example, one group of electrodes may fire at one frequency, while a second, different grouping of electrodes may fire at a frequency different from the first. In such a scenario, processing system 32 may include a rule to identify relevant patterns, correlations, fittings, matching, templates, or the like within the data set, data characterization and/or visual representation that identify a bimodal distribution. As stated above, upon identification of a bimodal distribution, processing system 32 may output a visual indicator corresponding to the different frequencies. The visual indicator may include an arrow on a display, text, color, highlighting or the like.

The descriptions above are merely example illustrations of the type of rules processing system 32 may include. It is understood that processing system 32 may include one or more additional rules corresponding to several diagnostic scenarios.

In at least some of the embodiments described above the disclosed methods assume analysis of sensed, collected, measured and transmitted electrical cellular data occurring during a single heartbeat and/or cardiac pulse. However, it is contemplated that any of the disclosed methods may be implemented across multiple beats or cardiac pacing time intervals. Further, data collected over multiple heart beats may be analyzed using statistical methodologies and applied to the disclosed methods. For example, activation times may be collected over a series of heart beats and/or pulses. A statistical distribution of the collected activation times may be calculated, analyzed and incorporated into disclosed methods.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

We claim:

1. A system for mapping electrical activity of a heart, comprising:
   a catheter comprising a distal end including a multiple electrode structure, the multiple electrode structure comprising a plurality of electrodes;
   a processor electrically coupled to the plurality of electrodes, wherein the processor is configured to:
      collect a set of signals from more than one of the plurality of electrodes, wherein more than one electrode of the plurality of electrodes collects the set of signals over a time period and includes signals from more than one heart cycle;
      calculate at least one propagation vector from the set of signals, wherein the propagation vector includes a direction and magnitude and wherein the magnitude is correlated to a characteristic of propagation of the electrical activity of the heart;
      generate a data set from the at least one propagation vector;
      generate a statistical distribution of the data set, wherein the statistical distribution includes the signals collected by the more than one electrode from the more than one heart cycle; and output to a display device a visual representation of the statistical distribution and the at least one propagation vector including the magnitude of the at least one propagation vector.

2. The system of claim 1, wherein to generate the statistical distribution of the data set, the processor is configured to generate a histogram of the data set.

3. The system of claim 2, wherein to generate the histogram of the data set, the processor is configured to generate a circular histogram.

4. The system of claim 2, wherein to output to a display device the visual representation of the statistical distribution, the processor is configured to output to the display device at least one circular histogram.

5. The system of claim 4, wherein to perform the algorithmic computation of the data set, the processor is configured to determine at least one of the following: standard deviation, entropy, kurtosis, skewness or the circular average of the data set.

6. The system of claim 1, the processor being further configured to perform an algorithmic computation of the data set.

7. The system of claim 6, wherein to perform the algorithmic computation of the data set, the processor is configured to generate a representative metric value for the data set.

8. The system of claim 7, wherein to generate the representative metric value, the processor is configured to generate a metric value for each of the plurality of electrodes across the time period.

9. The system of claim 8, the processor being further configured to output to a display device the representative metric values from each of the plurality of electrodes.

10. The system of claim 9, the processor being further configured to correlate one or more metric indicators to one or more representative metric values.

11. The system of claim 10, wherein each of the metric indicators correspond to a discrete metric interval, wherein the discrete metric intervals are subdivisions of an overall metric interval.

12. The system of claim 10, the processor being further configured to create a grid of the metric indicators for each of the plurality of electrodes.

13. The system of claim 1, wherein the at least one propagation vector includes a propagation angle, wherein to calculate the propagation vector, the processor is configured to utilize an activation and wherein to generate a data set, the processor is configured to define the data set to include the vector angle for each of the set of signals from the more than one of the plurality of electrodes.

14. The system of claim 2, wherein to generate a visual representation of the statistical distribution, the processor is configured to output to a display device one or more of a histogram, a circular histogram, a two-dimensional grid, a three-dimensional model, a three-dimensional surface and a propagation vector.

15. A method for mapping electrical activity of a heart, the method comprising:
advancing a catheter to a target region within a cardiac chamber, the catheter comprising a distal end including a multiple electrode structure, the multiple electrode structure comprising a plurality of electrodes, wherein the plurality of electrodes are coupled to a processor;
collecting a set of signals from at least one of the plurality of electrodes, wherein more than one electrode of the plurality of electrodes collects the set of signals over a time period and includes signals from more than one heart cycle;
calculating at least one propagation vector from the set of signals, wherein the propagation vector includes a direction and magnitude and wherein the magnitude is correlated to a characteristics of propagation of the electrical activity of the heart;
generating a data set from the at least one propagation vector;
generating a statistical distribution of the data set, wherein the statistical distribution includes the signals collected by the more than one electrode from the more than one heart cycle; and
displaying a visual representation of the statistical distribution and the at least one propagation vector including the magnitude of the at least one propagation vector, wherein displaying a visual representation includes displaying one or more of a confidence level, a reliability level and a stability level.

* * * * *